United States Patent
Maasen

(10) Patent No.: US 10,485,738 B2
(45) Date of Patent: Nov. 26, 2019

(54) TABLET FOR FLUORIDATING POTABLE WATER

(71) Applicant: K. C. Industries, L.L.C., Mulberry, FL (US)

(72) Inventor: Paul Maasen, St. Louis, MO (US)

(73) Assignee: K.C. Industries, LLC, Mulberry, FL (US)

( * ) Notice: Subject to any disclaimer, the term of this patent is extended or adjusted under 35 U.S.C. 154(b) by 0 days.

(21) Appl. No.: 16/205,274

(22) Filed: Nov. 30, 2018

(65) Prior Publication Data

US 2019/0175456 A1 Jun. 13, 2019

Related U.S. Application Data

(60) Provisional application No. 62/596,418, filed on Dec. 8, 2017.

(51) Int. Cl.
| | | |
|---|---|---|
| *A61K 8/02* | (2006.01) | |
| *A61K 8/21* | (2006.01) | |
| *A61K 8/46* | (2006.01) | |
| *C02F 1/68* | (2006.01) | |
| *A61K 8/92* | (2006.01) | |
| *A61K 8/36* | (2006.01) | |
| *A61Q 11/00* | (2006.01) | |
| *A61K 8/73* | (2006.01) | |

(52) U.S. Cl.
CPC .............. *A61K 8/0216* (2013.01); *A61K 8/21* (2013.01); *A61K 8/361* (2013.01); *A61K 8/466* (2013.01); *A61K 8/731* (2013.01); *A61K 8/922* (2013.01); *A61Q 11/00* (2013.01); *C02F 1/68* (2013.01)

(58) Field of Classification Search
None
See application file for complete search history.

(56) References Cited

FOREIGN PATENT DOCUMENTS

WO WO-2005030653 A1 * 4/2005 ............. A61K 33/16

* cited by examiner

*Primary Examiner* — Nannette Holloman
(74) *Attorney, Agent, or Firm* — Larson & Larson, P.A.; Justin P. Miller; Frank Liebenow

(57) ABSTRACT

A tablet for use in fluoridating potable water supplies in small municipalities and single point well systems. The tablet preferably contains sodium fluorosilicate, hydrogenated cottonseed oil, and magnesium stearate. The tablet is fed into a dispersal system into the water supply. In systems that treat approximately 150,000 to 600,000 gallons of water per day, the tablet will provide a target fluoride concentration between 0.5 and 0.7 ppm (mg/L).

16 Claims, 2 Drawing Sheets

TABLET FOR FLUORIDATING POTABLE WATER

CROSS-REFERENCE TO RELATED APPLICATION

This application is a continuation-in-part of U.S. Pat. App. Ser. No. 62/596,418, filed Dec. 8, 2017.

FIELD

This invention relates to the field of potable water treatment and more particularly to a recently-developed tablet that is used to fluoridate potable water sources, such as small Public Water Systems (PWS); sometimes referred to as Community Water Systems (CWS); generally serving up to 5,000 people, including single-point well systems, multi-point well systems and surface water systems (lakes, rivers, streams).

BACKGROUND

Regardless of age, ethnicity, or gender, optimally fluoridated community drinking water has clear individual and community health benefits. Properly fluoridated water helps prevent and slow tooth decay.

A 2016 Longitudinal Study examined a number of previous studies of Community Water Fluoridation (CWF) conducted between 1995 and 2013. The Longitudinal Study Research included a CWF Benefit/Cost analysis. (Economic Evaluation of Community Water Fluoridation: A Community Guide Systematic Review; Tao Ran, PhD, Community Preventive Services Task Force and Sajal Chattopadhyay, PhD. Am J Prev Med.—Author Manuscript available in PMCID: PMC6171335 PMC 2018 Oct. 4.)

The authors of the 2016 Longitudinal Study discovered or reiterated the following:
1. Dental costs were lower in communities with water fluoridation.
2. Per capita annual fluoridated water intervention ranged from $0.12 to $5.27 (adjusted for inflation to 2018 dollars) for communities with a population of at least 1,000.
3. Per capita, inflation-adjusted annual benefit ranged from $5.92 to $100.41.
4. Benefit/cost ratios ranged from $1.20 to $1 up to $146.46 to $1. Benefit/cost ratios improve with community population size.

Study authors concluded the recent evidence continues to indicate the economic benefit of community water fluoridation exceeds the intervention cost. (See PMCID: PMC6171335 PMC 2018 Oct. 4)

Furthermore, research has linked improved dental health to better overall health, especially for children. Properly fluoridated community water for children is associated with fewer dental carries, fewer trips to the ER, less missed school, fewer chronic infections, improved overall health, and improved self-confidence. Intervention early in life is associated with a lower need for drastic intervention later in life. (CDC Community Fluoridation Pages last updated Sep. 7, 2016 and accessed on Nov. 26, 2018.)

Today, roughly 70 to 75 percent of the US population is served by fluoridated community water systems. However, approximately 76 to 80 million Americans still do not have access to water with fluoride; the majority of those without access are in small towns or rural areas. (CDC Community Fluoridation Pages last updated Sep. 7, 2016 and accessed on Nov. 26, 2018.)

Healthy People, an organization that provides science-based, 10-year national objectives for improving the health of Americans, has set a goal to increase the availability of fluoridated water to 76 to 80 percent of the nation's population by 2020. To reach this aggressive goal, an additional 28 to 31 million people will need access to fluoridated community water.

To meet this goal, an improved fluoride delivery system for use by small municipalities must be developed. A tabletized form of sodium fluorosilicate adapted to commercially available feeder equipment will be a viable product for the small community and rural markets.

SUMMARY

The majority of the U.S. population not served by fluoridated water systems are in communities of 5,000 or less and in rural areas. The benefits of fluoridated water can be provided to these areas via a tablet containing fluoride and a delivery system that can release the recommended level of fluoride into the community water source.

Important considerations for choosing a fluoride chemical are quality, availability, cost—including the chemical, its transportation, and its storage, available or existing feeder equipment, operator training, and the type and size of water system.

The current fluoride market uses three chemicals for water fluoridation and all are rated as hazardous chemicals: Sodium Fluorosilicate, Fluorosilicic Acid, and Sodium Fluoride.

Sodium Fluorosilicate (SFS)—

SFS is the lowest cost chemical on a fluoride ("F") basis. It is used by approximately 17 percent of municipal fluoridating water systems in the United States. SFS is a dry product, making it easy to transport and store.

The procedure to create fluoridated water for an SFS designed system includes: feeding a bag of crystalline powder SFS into a hopper; dissolving the SFS in water; and then feeding the SFS solution into a potable water stream at the correct dosage.

Fluorosilicic Acid (FSA)—

FSA is a liquid product and is typically 76 percent water. It is only 18 percent fluoride ("F") versus 60 percent for SFS. FSA is used primarily by cities employing large systems to fluoridate their water supply.

FSA is not the best choice for small water systems or medium, multi-point water systems. Typically, when it is used by a small water system, it is supplied in five-gallon to fifty-gallon containers. These smaller packages require personal handling of the hazardous liquid by operators, creating the potential for spills and accidents. Furthermore, a distributor purchases the product in 4000-gallon tank trucks, which then must be repackaged into corrosion-resistant plastic containers. The containers must later be returned to that distributor. The result of so many steps is an increased cost. This increased cost, and the limited storage available in smaller facilities, makes FSA an impractical choice.

Sodium Fluoride (SF)—

SF has only been used for very small water systems. It is not the chemical of choice for most systems because of its availability and cost on a fluoride basis. There are no U.S. manufacturers and it has dusting problems. Less than 10 percent of all U.S. municipal water systems use SF.

Based on chemical attributes, cost, and availability, SFS is the preferred chemical for tablet formulation. The SFS tablet of the present disclosure has shown adequate strength and hardness, low sticking in the manufacturing process, adequate durability for shipping, and a long shelf life for storage.

The primary advantages to the consumer of the SFS tablet of the present disclosure are its ease of handling, the lack of dust, the ease of storage, and less exposure to the hazardous materials.

The SFS tablet and feeder system will allow small public water systems to fluoridate their water supply safely and reliably.

Example application of the SFS tablet includes tablet insertion into a feeder, such as a commercially available, flow-through swimming pool feeder. The feeder is installed in-line with a system that requires fluoridation. As water flows through the feeder, the water comes into contact with the inserted tablets and the tablets dissolve into the flowing water.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
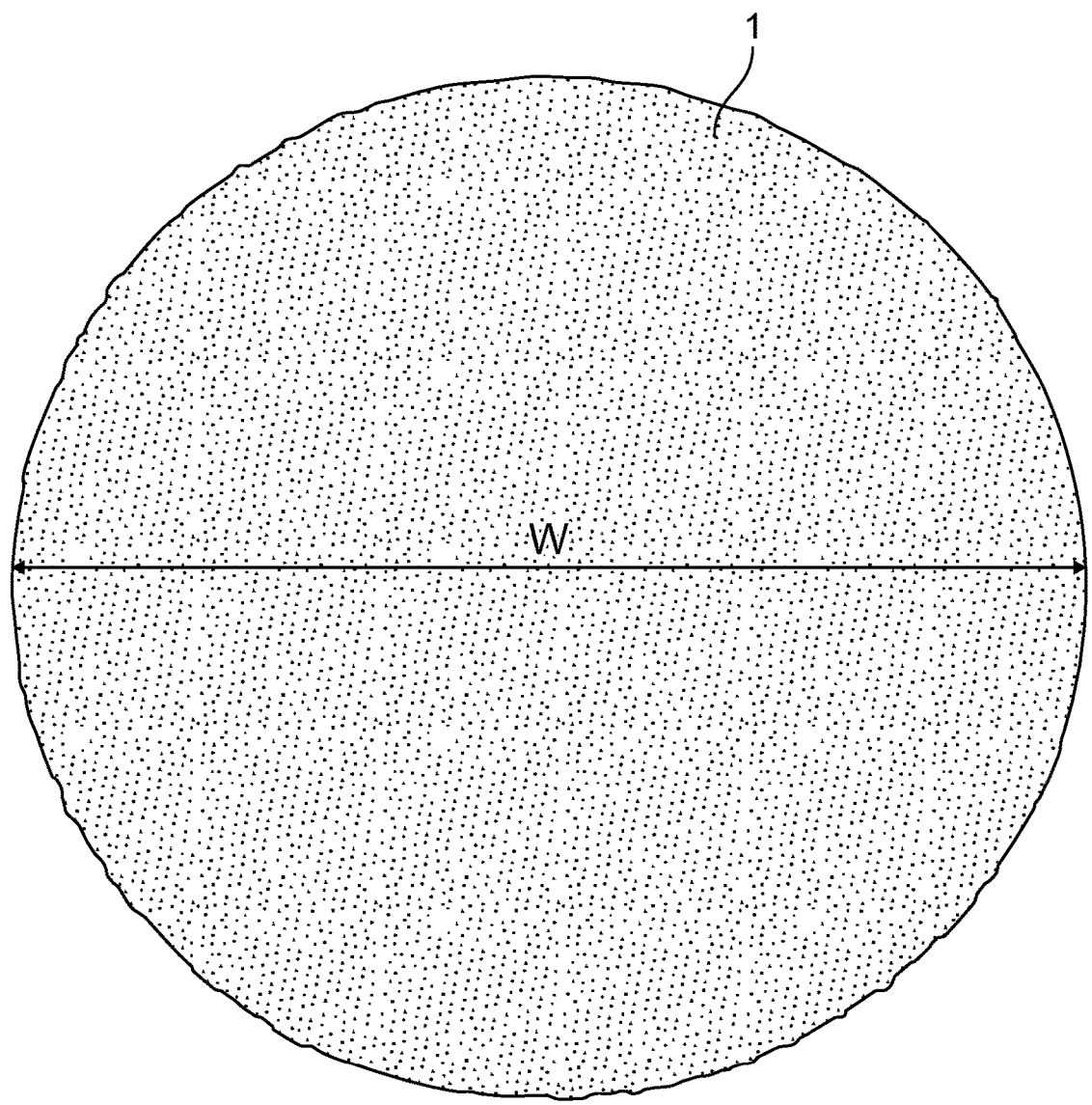
FIG. 1 illustrates a top view of an SFS tablet for use fluoridating potable water.

Reference will now be made in detail to the presently preferred embodiments of the invention, examples of which are illustrated in the accompanying drawings. Throughout the following detailed description, the same reference numerals refer to the same elements in all figures.

Figure 2:
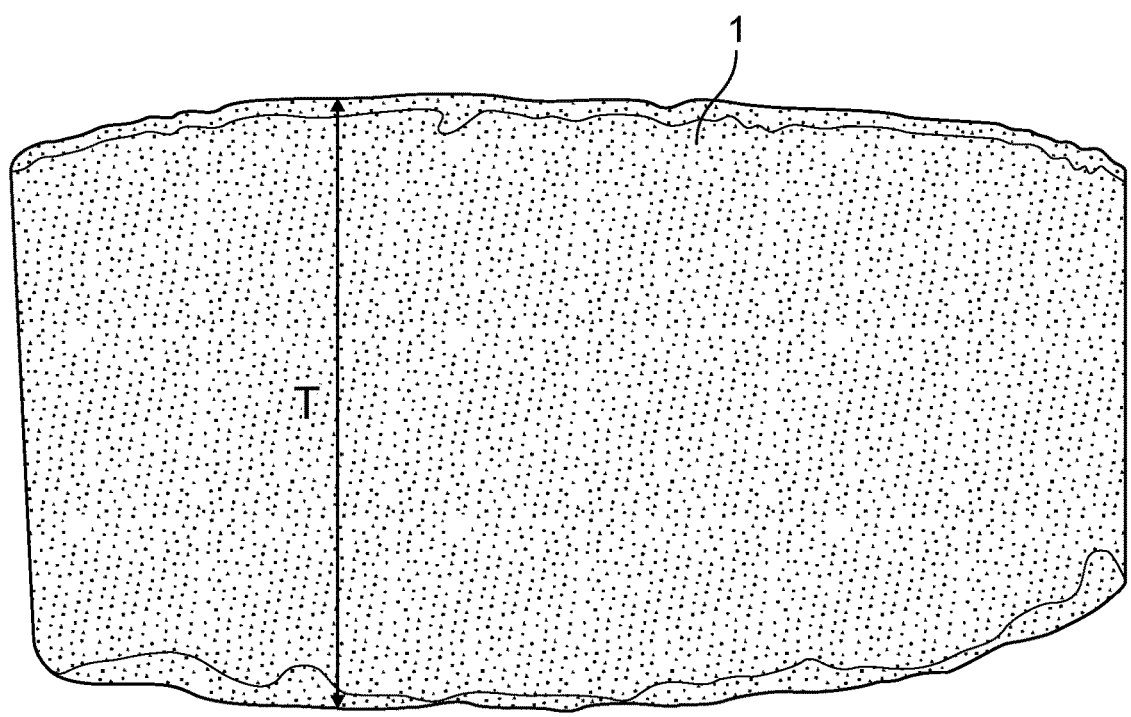
FIG. 2 illustrates a side view of an SFS tablet for use fluoridating potable water.

Referring to FIG. 1, a top view of an SFS tablet 1 is shown. Referring to FIG. 2, a side view of an SFS tablet 1 is shown.

An exemplary width W is 6.3 cm. An exemplary thickness T is 3 cm. Other widths and thicknesses are acceptable depending upon the dimensions of the feeder that will accept the tablets.

The SFS tablets 1 are comprised of sodium fluorosilicate, an excipient, and a punch release agent.

The excipient serves as a binder in tablet formation. The two preferred excipients are hydrogenated cottonseed oil and hydroxypropylcellulose.

The punch release agent allows tablets to be ejected from the tablet press more easily. Tablets without a punch release agent will require more pressure to eject, which leads to breaking or shearing of the tablets. Incorporation of calcium stearate powder at 0.5 weight percent into the formulations was found to greatly reduce the ejection pressure needed. The preferred punch release agents are magnesium stearate and calcium stearate.

Optionally, the tablets further include an anti-caking agent. SFS has clumping or caking issues if it stands more than a short time. Therefore an anti-caking agent, sodium alkylnaphthalenesulfonate, is optionally added to reduce this tendency.

The presence of sodium alkylnaphthalenesulfonate was expected to affect tablet integrity. To review, a study was performed comparing the strength of: SFS with sodium alkylnaphthalenesulfonate to SFS without sodium alkylnaphthalenesulfonate. Tablets were pressed at 18-20 tons. The tablets made without the sodium alkylnaphthalenesulfonate exhibited a break strength 40% higher (63.7 lbs compared to 45 lbs) than tablets made with sodium alkylnaphthalenesulfonate. Thus, the preferred embodiments do not include sodium alkylnaphthalenesulfonate.

Exemplary tablet formulations include:
1. 79.75 percent by weight SFS, 19.75 percent by weight hydrogenated cottonseed oil—a binding agent, and 0.5 percent by weight magnesium stearate—a punch release agent;
2. 88.5 percent by weight SFS, 11.0 percent by weight hydrogenated cottonseed oil, and 0.5 percent by weight magnesium stearate;
3. 88.0 percent by weight SFS, 11.5 percent by weight hydrogenated cottonseed oil, and 0.5 percent by weight magnesium stearate;
4. At least 80 percent by weight SFS, with the remainder being a binder, and the optional addition of a punch release agent at between 0.1 and 1.0 percent by weight.

Formulation 3 provided the best combination of a tablet that maintains structural integrity during production, storage, and transportation, while retaining high dissolution rates when it comes in contact with water.

Notwithstanding the above, the following chemicals may serve as binding and/or release agents depending upon the percentage used within the tablet:

Hydrogenated Vegetable Oil
Hydrogenated Cottonseed Oil
Magnesium Stearate
Calcium Stearate
Starch
Hydroxypropyl Cellulose
Sodium Alkylnaphthalenesulfonate
Method of Making Tablets Each batch of tablets has a total weight between 100 and 500 grams. Ingredients were charged to a laboratory stainless steel v-shaped blender.

An exemplary mixture batch for 100 grams of formulation 1 will include: 79.75 g SFS, 19.75 g hydrogenated cottonseed oil, and 0.5 g punch release agent.

An exemplary mixture batch for 200 grams of formulation 2 will include: 177 g SFS, 22 g hydrogenated cottonseed oil, and 1 g punch release agent.

After adding the ingredients, the blender is sealed and rotated at 23 rpm for 5 minutes.

Then, a 50 gram portion of the blend is weighed and placed in a round, two-inch diameter, straight-wall die fitted with lower and upper punches.

The 50 g portion of the blend is then compressed at tonnages from 10 to 40 tons.

The result is a tablet containing SFS that is used to fluoridate water supplies.

Observations

The first formulation level of 79.75 percent by weight SFS, 19.75 percent by weight hydrogenated cottonseed oil, and 0.5 percent by weight magnesium stearate, a punch release agent was found to have a balance of tablet hardness and easy punch release however the formulation cost was higher.

The second formulation delivered the most predictable fluoride ion ($F^{-1}$) into the water. The decrease in excipient concentrations has benefits for the manufacturing cost of the tablet as well as giving the final product more of the key ingredient—SFS.

CONCLUSION

The above formulations exhibited and maintained ideal physical integrity during the testing period with no visual observation of release of sodium fluorosilicate crystals from the tablet matrix and displayed preferential and consistent dissolution rates analogous to other recreational water treatment tablets. Testing of the above formulations demonstrated the release of the active ingredient and the desired end product—fluoride ion ($F^{-1}$) concentrations sufficient to effectively treat small potable water treatment systems.

Using the improved SFS tablet formulations, potable water treatment systems ranging from approximately 150,000 to 600,000 gallons per day can be effectively treated to a target fluoride ($F^{-1}$) concentration of 0.5 to 0.7 mg/L (ppm).

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A tablet for use fluoridating municipal water sources, the tablet comprising:
    88.0 percent by weight of sodium fluorosilicate;
    11.5 percent by weight of binder; and
    0.5 percent by weight of punch release agent.
2. The tablet of claim 1 wherein the binder is selected from the group consisting of: hydroxypropylcellulose and hydrogenated cottonseed oil.
3. The tablet of claim 1 wherein the punch release agent is selected from the group consisting of: magnesium stearate and calcium stearate.
4. The tablet of claim 1 wherein the binder is selected from the group consisting of: magnesium tearate, calcium tearate, starch, hydroxypropyl cellulose, and sodium alkylnaphthalenesulfonate.
5. The tablet of claim 1 wherein the punch release agent is selected from the group consisting of: hydrogenated vegetable oil, hydrogenated cottonseed oil, starch, hydroxypropyl cellulose, and sodium alkylnaphthalenesulfonate.
6. A tablet for treating municipal potable water sources, the tablet comprising:
    sodium fluorosilicate in an amount of from about 80.0 wt. % to about 88.5 wt. %;
        the sodium fluorosilicate acting as a water fluoridation chemical;
    hydrogenated cottonseed oil in an amount from about 11.0 wt. % to 20 wt. %;
        the hydrogenated cottonseed oil acting as a binder.
7. The tablet of claim 6, further comprising:
    a punch release agent in an amount from 0.1 wt. % to about 1.0 wt. %.
8. The tablet of claim 7, wherein:
    the punch release agent is magnesium stearate.
9. The tablet of claim 7, wherein:
    the punch release agent is calcium stearate.
10. A tablet to provide enhanced dental benefits to small municipalities by increasing fluoride ion concentration in a water supply, the tablet comprising:
    sodium fluorosilicate;
    a binder; and
    a punch release aid.
11. The tablet of claim 10, wherein the sodium fluorosilicate further comprises an anti-caking agent.
12. The tablet of claim 11, wherein the anti-caking agent is sodium alkylnaphthalenesulfonate.
13. The tablet of claim 10 wherein the binder is selected from the group consisting of: hydroxypropylcellulose and hydrogenated cottonseed oil.
14. The tablet of claim 10 wherein the punch release agent is selected from the group consisting of: magnesium stearate and calcium stearate.
15. The tablet of claim 10 wherein the binder is selected from the group consisting of: magnesium stearate, calcium stearate, starch, hydroxypropyl cellulose, and sodium alkylnaphthalenesulfonate.
16. The tablet of claim 10 wherein the punch release agent is selected from the group consisting of: hydrogenated vegetable oil, hydrogenated cottonseed oil, starch, hydroxypropyl cellulose, and sodium alkylnaphthalenesulfonate.

* * * * *